United States Patent [19]
Cohen et al.

[11] 4,205,191
[45] May 27, 1980

[54] HYDROCARBON HYDROGENATION USING ZERO VALENT METAL CATALYSTS

[75] Inventors: Murray S. Cohen, Convent Station, N.J.; Jan G. Noltes, Huis Ter Heide; Gerard van Koten, Bilthoven, both of Netherlands

[73] Assignee: Borg-Warner Corporation, Chicago, Ill.

[21] Appl. No.: 962,268

[22] Filed: Nov. 20, 1978

Related U.S. Application Data

[62] Division of Ser. No. 827,278, Aug. 24, 1977, Pat. No. 4,152,303.

[51] Int. Cl.² .......................... C07C 5/02; C07C 5/04; C07C 5/06; C07C 5/08
[52] U.S. Cl. .................................... 585/250; 585/261; 585/262; 585/267; 585/269; 585/277
[58] Field of Search ............... 585/250, 261, 262, 267, 585/269, 277

[56] References Cited

U.S. PATENT DOCUMENTS 4,152,303  5/1979  Cohen et al. .......................... 252/454

OTHER PUBLICATIONS

Popov et al., Chem. Ab. 84:73771u.
Alchudzhau et al., Chem. Ab. 71:12280v.
Alchudzhau et al., Chem. Ab. 72:66452s.
Popov et al., Chem. Ab. 77:18935h.

*Primary Examiner*—Veronica O'Keefe
*Attorney, Agent, or Firm*—Joseph Shekleton

[57] ABSTRACT

A process for the preparation of novel zero-valent metal catalysts. The catalysts are prepared by the reaction of an organic metal cluster compound wherein one of the metals is lithium with a complex of a metal halide and a ligand. The catalyst may, if desired, be deposited on a support such as alumina or silica. It is effective to catalyze the hydrogenation of organic compounds such as benzene, styrene and the like.

6 Claims, No Drawings

HYDROCARBON HYDROGENATION USING ZERO VALENT METAL CATALYSTS

This application is a division of application Ser. No. 827,278, filed Aug. 24, 1977, now U.S. Pat. No. 4,152,303.

The invention of this application relates to a novel catalyst and its method of preparation. More particularly, it relates as indicated to a zero valent metal catalyst; the catalyst is effective to promote the hydrogenation of aromatic, olefinic and acetylenic compounds, as well as other reactions normally susceptible to catalysis.

Ten Hoedt et al, J. Organomet. Chem. 133 (1977) 113-121, show the preparation of certain mixed-organocopper cluster compounds by the ligand substitution reaction of $Ar_4Cu_6Br_2$ with two equivalents of LiC-CR.

Popov et al, C.A. 84: 73771w, suggest that the effectiveness of a rhodium-alumina catalyst in the hydrogenation of benzene is directly proportional to the proportion of rhodium in the catalyst. The temperature of the hydrogenation ranged from 100° C. to 160° C.

Alchudyhan et al, C.A. 71 12280v, studied the temperature dependence of the rate of benzene hydrogenation on the rhodium/silica catalyst. The activity was studied at 200° C., 160° C., 140° C., 115° C., 90° C. and 70° C. The activity-temperature curve showed a maximum at 110° C. Also, the activity of Group VIII metals was shown to decrease in the series rhodium ruthenium platinum palladium.

Alchudyhan et al, C.A. 72: 66452s, show the catalysis of benzene hydrogenation by a silver rhodium mixture and also by a rhodium gold mixture.

Bryce-Smith et al, Ger. Offen. 2, 117, 439, show the preparation of improved transition metal catalysts by treating a salt of the metal with the adduct of an aromatic compound and an alkali metal or alkaline earth metal (other than magnesium).

Popov et al, C.A. 77: 18935h, show the hydrogenation of benzene in the presence of several mixed catalysts including platinum-ruthenium, rhodium-ruthenium, platinum-palladium, palladium-rhodium and platinum-rhodium. At 160° C., the most effective catalyst was found to be a 90:10 palladium-ruthenium mixture.

Van Koten et al, J. Organomet. 1975, 85(1) 105-14, propose a cyclic organic copper cluster structure which is polymeric in nature.

The invention of the present application is a process for the preparation of a zero valent metal catalyst comprising reacting an organic metal cluster compound wherein one of the metals of said cluster compound is lithium, with a metal halide complex of the formula $MX_aL_b$ wherein M is a transition metal, X is halogen, L is an organic ligand, a is 1-3 and b is 1-4, in a hydrocarbon solvent. The invention also includes the zero valent metal catalyst thus prepared and its use in the catalysis of hydrogenation reactions. The process preferably is carried out in a dry, oxygen-free atmosphere. The atmosphere may be, e.g., nitrogen, ethylene or carbon monoxide.

The metal cluster compound also contains, in addition to lithium, a group 1B metal. Gold is preferred although silver and copper are also quite satisfactory. A third metal may in some instances be present also. Thus, a metal cluster compound may contain lithium, and two different group IB metals; other metals may also be present although in the more usual cases only two metals will be present, one being lithium and the other a group IB metal. The composition of the metal cluster compound may be shown by the formula $Ar_{x+y}M_xLi_y$ where Ar is aromatic hydrocarbyl such as phenyl or alkylphenyl, i.e., tolyl, mesityl, etc., M is a group IB metal, x and y are 1-3, and x+y is 2-8. Preferably, x+y is 4.

The process is carried out very simply, merely by mixing the reactants at room temperature, i.e. from about 20° C. to about 30° C. A reaction occurs at once. The zero valent metal product may be used as such in a catalytic hydrogenation, or it may be deposited on a support and isolated by decanting the hydrocarbon solvent away from the solid product. The support may be any of those commonly used in catalytic chemistry, viz., alumina, silica, clay and the like.

The metal halide complex is as indicated a transition metal halide complex. Metals of groups IIIB, IVB, VB, VIB, VIIB and VIII are contemplated. Rhodium is preferred; platinum, palladium, cobalt, nickel, iridium and ruthenium are also specifically contemplated. The halide may be fluorine, chlorine, bromine or iodine. Chlorine is preferred. The organic ligand is construed broadly; specific illustrative embodiments include ethylene, carbon monoxide, triphenyl phosphine and diethyl ether. Examples of metal halide complexes include $RhCl(CH_2=CH_2)_2$, $RhBr(CO)_2$, $NiCl_2(C_2H_5OC_2H_5)_4$, etc.

The process is carried out in a solvent. The reactants may not be completely soluble in the solvent, nor is the zero valent metal product, and agitation of the process mixture is highly desirable. Suitable solvents include benzene, toluene, xylene, ethylbenzene, pentane, cyclohexane and, in fact, any hydrocarbon solvent which is normally liquid, i.e., liquid at about room temperature.

The hydrogenation reactions which are catalyzed by the zero valent metal products herein may in most instances be carried out at room temperature and at ordinary pressures. Aromatic compounds, i.e., the aromatic ring, can be hydrogenated merely by introducing hydrogen into a reaction vessel containing the aromatic compound. Benzene and naphthalene, for example, can be hydrogenated in this fashion, benzene yielding cyclohexane and naphthalene yielding tetralin. Olefinic compounds can also be hydrogenated under similar conditions. Styrene, for example, can be converted to ethylbenzene and then to ethylcyclohexane. Stilbene can be converted to 1,2-diphenylethane and then to 1,2-dicyclohexylethane. Phenylacetylene can be hydrogenated likewise to ethylbenzene, and then to ethylcyclohexane.

The organic metal cluster compounds may be prepared by known methods. An aryl lithium compound such as tolyllithium is reacted with an aryl copper compound or half an equivalent amount of cuprous halide, for example, to form a metal cluster product whose composition is indicated by the formula $Ar_4Cu_2Li_2$. The Ar, which is toluene in the above example, may also be benzene, xylene mesitylene, etc. The method of preparation is illustrated by Examples 1-3.

EXAMPLE 1

A solution of 980 mg. (10 mmols) of p-tolyllithium in 15 ml. of diethylether is added to a suspension of 1.54 g. (10 mmols) of p-tolylcopper, yielding a clear pale yellow solution. The solution is stirred for 10 minutes whereupon a yellow precipitate is formed. The mixture is stirred for an additional 30 minutes, cooled to −40° C. and the liquid decanted from the solid. The solid residue is washed with 15 ml. of chilled (−40° C.) diethylether and two 50-ml. portions of pentane. The dried, pale yellow solid weighs 2.1 g. (64% of the theory). It ignites spontaneously in air and decomposes in nitrogen at 135° C. It is identified by NMR and its molecular weight (found: 630; calc.: 653) as having the formula p-Tol$_4$Cu$_2$Li$_2$.2(C$_2$H$_5$)$_2$0.

EXAMPLE 2

To a yellow solution of 1.54 g. (10 mmols) of p-tolylcopper in 40 ml. of benzene there is added, with stirring, 980 mg. (10 mmols) of p-tolyllithium. The solution soon deposits a pale yellow precipitate and the mixture is stirred for an additional 30 minutes. The colorless liquid is decanted; its NMR spectrum shows the presence only of a minor amount of p,p-bitolyl. The solid residue is washed with two 60-ml. portions of benzene and two 60-ml. portions of pentane. The solid is dried, yielding 2.3 g. (92% of the theory) of a pale yellow powder. It ignites spontaneously in air. It is soluble in diethyl ether with which it easily forms the etherate product of Example 1.

The di-(o-tolyl) copperlithium, having the formula o-Tol$_4$Cu$_2$Li$_2$, may be prepared in the same manner.

EXAMPLE 3

To a stirred solution of 1.96 g. (20 mmols) of p-tolyllithium there is added portionwise 4.94 g. (10 mmols) of gold chloride-triphenylphosphine complex (AuCl.P(Ph)$_3$). The solution becomes yellow and a white precipitate (LiCl) is deposited. The mixture is stirred for an additional 30 minutes, then the yellow liquid is decanted from the lithium chloride and the decanted liquid evaporated at reduced pressure to a yellow-brown paste. This paste is washed with three 100-ml. portions of pentane and the residual white solid is dried in air. The dried material weighs 4.1 g. (90% of the theory). It decomposes in nitrogen at 60° C. and is soluble in diethyl ether and benzene. Its NMR spectrum is consistent with the formula p-tol$_4$Au$_2$Li$_2$.(C$_2$H$_5$OC$_2$H$_5$)$_2$.

Examples 4 and 5 illustrate the process of the invention, i.e., preparation of zero valent metal catalysts.

EXAMPLE 4

To a suspension of 504 mg. (1 mmol) of p-tolylcopper-lithium (p-tol$_4$Cu$_2$Li$_2$) in 30 ml. of benzene under nitrogen, there is added with stirring 1.0 mmol of rhodium chloride-ethylene complex (RhCl—(CH$_2$=CH$_2$)$_2$). The suspension becomes dark at once, indicating the formation of (p-tol)$_4$Cu$_2$Rh$_2$, which decomposes spontaneously with the formation of Cu°/Rh°.

EXAMPLE 5

To a suspension of 0.5 mmol of p-tolylgoldlithium etherate (p-tol)$_4$Au$_2$Li$_2$(C$_2$H$_5$OC$_2$H$_5$)$_2$ in 30 ml. of benzene under nitrogen, there is added with stirring 1.0 mmol of rhuthenium chloride.ethylene complex (RhCl.(CH$_2$=CH$_2$)$_2$). Immediately, the colour of the suspension darkens, indicating the formation of (p-tol)$_4$Au$_2$Rh$_2$, followed immediately by its decomposition to the desired Au°/Rh°.

EXAMPLE 6

The preparation of Rh° may be accomplished in a similar manner, reacting p-tolLi with a rhodium halide complex such as the ethylene or diethyl ether complex. An unstable intermediate similar to the above tetrametal structure is formed and then the desired Rh° metal.

Examples 7 and 8 show the use of the zero valent metal products of the process of the invention as a catalyst in the hydrogenation of benzene.

EXAMPLE 7

The product mixture of Example 4, containing Cu°/Rh° suspended in 30 ml. of benzene, is stirred and treated with hydrogen, displacing the nitrogen. Immediately there is a rapid consumption of hydrogen. A pressure of 1.05 atmospheres of hydrogen is maintained and the temperature is kept at 20° C. Hydrogen is consumed at a rate of 18 ml./minute quite uniformly throughout a period of six hours, at which point a total of 6500 ml. of hydrogen has reacted. NMR spectre show the conversion of 27% of the benzene to cyclohexane.

EXAMPLE 8

The product mixture of Example 5, containing Au°/Rh° suspended in 30 ml. of benzene, is stirred and treated with hydrogen, replacing the nitrogen, so as to maintain a constant pressure of 1.05 atmosphere of hydrogen. The temperature is kept at 20° C. Under these conditions hydrogen is consumed uniformly over a period of two hours at a rate of 50 ml./minute. At this point, 6500 ml. of hydrogen has been consumed. NMR spectre show that about 30% of the benzene is converted to cyclohexane. The hydrogenation is continued the following day under the same conditions for an additional two hours, with the same results. A total of 13,000 ml. of hydrogen is consumed; the total yield of cyclohexane is about 58% of the theory.

Naphthalene, stilbene, styrene phenylacetylene and other aromatic, olefinic and acetylenic compounds may be hydrogenated similarly.

All parts and percentages herein are by weight unless otherwise expressly stated.

We claim:

1. A process for the hydrogenation of aromatic, olefinic and acetylenic compounds comprising treating such compounds with hydrogen in the presence of a zero-valent metal catalyst prepared by reacting an organic metal cluster compound of the formula Ar$_{x+y}$M$_x$Li$_y$ where Ar is aromatic hydrocarbyl, M is a group 1B metal, and x and y are 1–4, with a metal halide complex of the formula TX$_a$L$_b$ where T is a transition metal, X is halogen, L is an organic ligand, b is 1–4, and a is 1–3, in a hydrocarbon solvent.

2. The process of claim 1 wherein the hydrogenation is carried out at about room temperature.

3. The process of claim 1 wherein the compound to be hydrogenated is aromatic.

4. The process of claim 1 wherein the compound to be hydrogenated is olefinic.

5. The process of claim 1 wherein the compound to be hydrogenated is acetylenic.

6. The process of claim 1 wherein the hydrogenation is carried out at about atmospheric pressure.

* * * * *